United States Patent [19]

Mágó neé Karácsony et al.

[11] 4,299,836
[45] Nov. 10, 1981

[54] NOVEL ERGOL-8-ENE AND ERGOLIN COMPOUNDS AND PROCESS FOR PREPARING SAME

[75] Inventors: Erzsébet Mágó neé Karácsony; Lajos Toldy; József Borsy; László Tardos; Ildikó Király; András Rónay, all of Budapest, Hungary

[73] Assignee: Richter Gedeon Vegyeszeti Gyar Rt., Budapest, Hungary

[21] Appl. No.: 167,341

[22] Filed: Jul. 10, 1980

[30] Foreign Application Priority Data

Jul. 12, 1979 [HU] Hungary ............................ GO 1452

[51] Int. Cl.³ .................... A61K 31/48; C07D 457/02
[52] U.S. Cl. ........................................ 424/261; 546/67
[58] Field of Search ........................... 546/67; 424/261

[56] References Cited
FOREIGN PATENT DOCUMENTS
959261 5/1964 United Kingdom .................. 546/67

OTHER PUBLICATIONS
Wagner et al., Synthetic Organic Chemistry, (New York, 1953), pp. 822-823.

Primary Examiner—Alton D. Hollins
Attorney, Agent, or Firm—Keil & Witherspoon

[57] ABSTRACT

The invention relates to new ergol-8-ene and ergoline derivatives of the general formula /I/

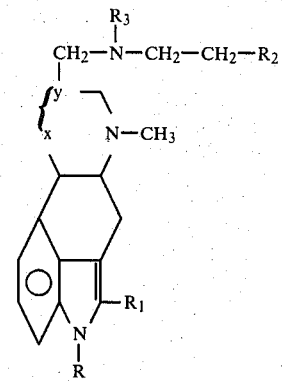

wherein
$\overline{x\,y}$ stands for —CH=C= or —CH$_2$—CH= group,
R stands for hydrogen atom or methyl group,
$R_1$ stands for hydrogen or halogen atom,
$R_2$ stands for lower alkylsulfonyloxy group, phenylsulfonyloxy group optionally substituted with a lower alkyl group, or azido group,
$R_3$ stands for lower alkylsulfonyloxy group or phenylsulfonyloxy group optionally substituted with a lower alkyl group, and acid addition salts thereof. These compounds can be prepared from compounds of the general formula II

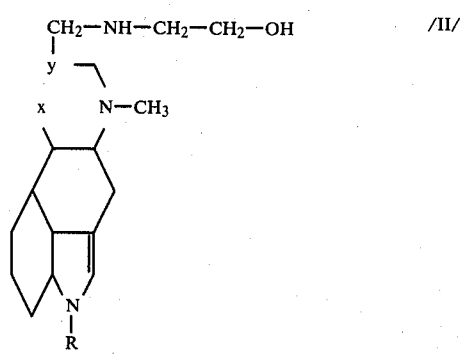

wherein x y and R are as defined above, by reacting at least two equivalents of a lower alkylsulfonic acid chloride or phenylsulfonic acid chloride substituted with lower alkyl group. The resulting compound can be reacted with an alkali metal azide, and, if desired, the compound obtained is treated with a halogenating agent to form the 2-halogenide derivative, and, if desired, any resulting compound of general formula I is treated with an acid to form a therapeutically acceptable acid addition salt, or the free base is liberated from a salt.

The compounds of general formula I possess valuable antiserotonine, antidepressant, dopamine receptor stimulant and hypotensive effects.

5 Claims, No Drawings

NOVEL ERGOL-8-ENE AND ERGOLIN COMPOUNDS AND PROCESS FOR PREPARING SAME

This invention relates to new ergol-8-ene and ergoline derivatives of general formula /I/

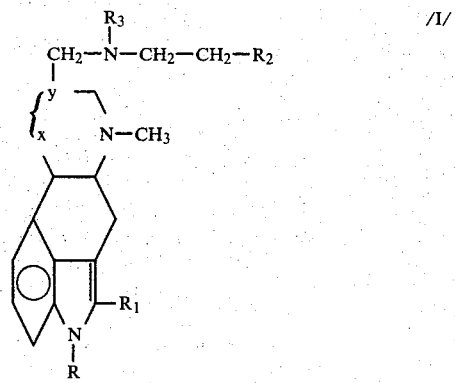

wherein
- $\overline{xy}$ stands for —CH=C= or —CH$_2$—CH= group,
- R stands for hydrogen atom or methyl group,
- R$_1$ stands for hydrogen or halogen atom,
- R$_2$ stands for lower alkylsulfonyloxy group, phenylsulfonyloxy group optionally substituted with a lower alkyl group, or azido group,
- R$_3$ stands for lower alkylsulfonyloxy group or phenylsulfonyloxy group optionally substituted with a lower alky group, and acid addition salts thereof.

As known, in the last few years several semisynthetic compounds with ergolene or ergoline skeleton were synthetized and introduced into the therapy beside the natural ergot alkaloids /P. A. Stadler and P. Stütz "The Alkaloids Chemistry and Physiology", Academic Press, New York, 1975, pp. 32–36/. Examples of these semisynthetic compounds are: 6-methyl-8β-acetylaminomethyl-ergoline (Uterdina), possessing specific uterotropic activity; 1,6-dimethyl-8β-[(benzyloxycarbonyl)-aminomethyl]-ergoline (Metergoline) which is a potent antiserotonine agent; 1-methyl-10β-methoxy-dihydrolysergol-5'-bromo-nicotinate (Nicergoline) which is a hypotensive drug; and 2-chloro-6-methyl-8β-cyanomethyl-ergoline /Lergotril/ which is a potent inhibitor of prolactine secretion. Among the compounds hitherto synthetized, no sulfonic-ester-, sulfonamide- or azido-derivatives are known so far.

The aim of the invention was to produce new ergol-8-ene and ergoline derivatives of sulfonic-ester-, sulfonamide- or azido-type, possessing significant physiological activities.

The invention is based on the recognition that the derivatives of general formula I, wherein the substituents are as defined above, possess valuable therapeutic properties. Furthermore, it has been found that these derivatives can be prepared from compounds of general formula II

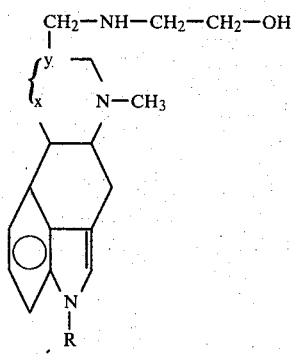

wherein $\overline{xy}$ and R are as defined above. The new ergol-8-ene and ergoline derivatives of general formula I, wherein x y, R, R$_1$, R$_2$ and R$_3$ are as defined above, and the acid addition salts thereof can be prepared by reacting a compound of general formula II, wherein x y and R are as defined above, with at least two equivalents of a lower alkylsulfonyl chloride or a phenylsulfonyl chloride optionally substituted with a lower alkyl group, and, if desired, reacting the resulting compound with an alkali metal azide, and, if desired, converting the resulting compound into a 2-halogenated derivative by reacting it with a halogenating agent, and, if desired, converting any resulting compound of general formula I into a therapeutically acceptable acid addition salt by reacting it with a suitable acid, or liberating the free base from a salt.

The compounds of general formula, II wherein $\overline{xy}$ and R are as defined above, applied as starting substances in the process of the invention can be prepared in the way as described in the Hungarian patent specification No. 170,271.

According to a preferred method of the invention a compound of general formula II is dissolved in pyridine and two equivalents of methanesulfonyl chloride are added at 0° to 5° C. Thereafter the reaction mixture is stirred at room temperature; the progress of reaction is monitored by thin-layer chromatography. After the reaction has terminated the product is separated and, if desired, converted into an acid addition salt. Maleic acid, tartaric acid or hydrochloric acid are preferred as salt-forming agents.

According to another method one can proceed by dissolving a compound of general formula I, wherein $\overline{xy}$, R, and R$_1$ are as defined above, while R$_2$ and R$_3$ represent a lower alkyl-sulfonyloxy group or a phenylsulfonyloxy group optionally substituted with a lower alkyl group, in dilute methylcellosolve (2-methoxyethanol), carbitol (2-/2-ethoxy-ethoxy/-ethanol), ethanol, methanol, dioxane or dimethyl formamide, and by admixing thereafter sodium azide. Then the reaction mixture is warmed for several hours. The progress of reaction is monitored by thin-layer chromatography. After the reaction has terminated the product is separated and, if desired, converted into an acid addition salt.

Still another method is to dissolve a compound of general formula I, wherein R$_1$ stands for hydrogen atom, in anhydrous dioxane, and to react it with N-bromo-succinimide at room temperature. The resulting product is purified by column chromatography. If desired, the product can be converted into an acid addition salt.

Some of the compounds of general formula I possess serotonine receptor antagonist properties, whilst other compounds exert antidepressant, dopamine receptor stimulant or hypotensive effects. The serotonine antagonist effect could be detected both under in vitro and in vivo conditions. In smooth muscle preparations, very low concentrations of the compounds are in vitro capable of antagonizing the contractile effect of serotonine in competitive manner. These compounds administered either parenterally or orally are highly effective in antagonizing the oedema-inducing effect of serotonine in vivo.

Compounds of general formula I, possessing remarkable antiserotonine activity in the oedema-test, are as follows:

1,6-dimethyl-8[(N-methanesulfonyl,N-azidoethyl)-aminomethyl]-ergol-8-ene-tartarate /Example 4/;

6-methyl-8-[(N-methanesulfonyl, N-azidoethyl)-aminomethyl]-ergoline hydrogen maleate /Example 7/;

1,6-dimethyl-8-[(N-methanesulfonyl, N-methanesulfonyloxy-ethyl)-aminomethyl]-ergoline hydrogen maleate /Example 9/;

1,6-dimethyl-8-[(N-methanesulfonyl, N-azidoethyl)-aminomethyl]-ergoline hydrogen maleate /Example 10/;

2-bromo-1,6-dimethyl-8-[(N-methanesulfonyl, N-azidoethyl)-aminomethyl]-ergoline tartarate /Example 11/.

The potency of some of these derivatives attains or even surpasses that of the reference substance Methysergide (1-methyl-d-lysergic acid-/+/-butanolamide-2-hydrogen maleate). Of these active derivatives, the compound specified in Example 10 (1,6-dimethyl-8-[(N-methanesulfonyl, N-azidoethyl)-aminomethyl]-ergoline hydrogen maleate) is more potent than Methysergide upon oral administration. The pharmacological data are presented in Table 1.

TABLE 1

| | Antiserotonine activity | | |
|---|---|---|---|
| | | In vivo test ED$_{50}$ (mg/kg) 50% inhibition of serotonine induced oedema | |
| Compound Example No. | In vitro test ED$_{50}$ (g/ml) | s.c. | p.o. |
| 4 | 5 × 10$^{-10}$ | 0.22 | 3.7 |
| 7 | 1 × 10$^{-9}$ | 0.29 | 1.7 |
| 9 | 5 × 10$^{-8}$ | 0.082 | 1.0 |
| 10 | 1 × 10$^{-9}$ | 0.042 | 0.47 |
| 11 | 5 × 10$^{-8}$ | 0.3 | 2.0 |
| Methysergide | 5 × 10$^{-9}$ | 0.026 | 0.64 |

The in vitro antiserotonine activity was determined in rat uterine horn preparation according to the method described by J. H. Gaddum and L. A. Hammed (Brit. J. Pharmacol. 9, 240 /1954/). For the in vivo studies the rat paw-oedema test was applied as described by I. L. Bonta (Arch. int. Pharmacodyn. 132, 147 /1961/).

Some representatives of the new compounds of general formula I exhibit remarkable antidepressant effects. Thus, the efficacy of the compound specified in Example 1 (6-methyl-8-[(N-methanesulfonyl, N-methanesulfonyloxyethyl)-aminomethyl]-ergol-8-ene hydrogen maleate) is equal to, whilst the potency of the compound described in Example 2 (6-methyl-8-[(N-methanesulfonyl, N-azidoethyl)-aminomethyl]-ergol-8-ene hydrogen maleate) is higher than that of Imipramine [5-/3-dimethylamino-propyl/-10,11-dihydro-5H-dibenzo/b,f/-azepine]. The compounds are effective upon oral administration as well. Furthermore, they are not toxic, and their antidepressant effect is dose-dependent. The results are listed in Table 2.

| | Antidepressant activity | | | |
|---|---|---|---|---|
| Compound (Example No.) | Dose (mg/kg) p.o. | Δt °C. | LD$_{50}$, mg/kg i.p. | p.o. |
| 1 | 10 | +4.1 | 100 | 100 |
| 2 | 10 | +6.5 | 100 | 100 |
| Imipramine | 10 | +5.2 | 115 | 666 |

The antidepressant activity was assessed by measuring the antagonism of reserpine-induced hypotermy in mice. The change in body temperature (Δt) was detected as compared to the control animals (B. M. Askew, Life Sci. 10, 725 /1963/). The acute toxicity data /LD$_{50}$/ were determined on mice; the evaluation was performed 24 hours after the administration of the compounds (J. T. Litchfield and F. Wilcoxon, J. Pharmacol. exp. Ther. 96, 99 /1949/).

Among the new compounds of general formula I the derivative specified in Example 2 (6-methyl-8-[(N-methanesulfonyl-N-azidoethyl)-aminomethyl]-ergol-8-ene hydrogen maleate) prossesses dopamine receptor stimulant activity. The efficacy of the compound is close to that of Bromocryptine (2-bromo-α-ergocryptine) in vitro whereas under in vivo conditions its potency is higher than that of the reference substance. The pharmacodynamic effects of the new derivative could also be detected upon oral administration. The results of the test are listed in Table 3.

TABLE 3

| | Dopamine receptor stimulant activity | | | |
|---|---|---|---|---|
| | | In vivo test Antagonism of Haloperidol effect in rats | | |
| Compound (Example No.) | In vitro test Mouse vas deferens ID$_{50}$(M/l) | Dose (mg/kg) | Inhibition (%) s.c. | p.o. |
| 2 | 5 × 10$^{-8}$ | 3.0 | 68.7 | — |
| | | 10.0 | 92.2 | 38.9 |
| | | 30.0 | — | 48.2 |
| Bromocryptine | 2 × 10$^{-8}$ | 10.0 | 26.2 | 25.9 |
| | | 30.0 | 34.2 | 54.8 |

The dopamine receptor stimulant activities in vitro were determined on electrically stimulated mouse vas deferens preparation (J. Hughes et al., Brit. J. Pharmacol. 53, 371–381 /1975/).

The in vivo measurements were performed on rats. The antagonism of narcosis-(Hexobarbital Na, 50 mg/kg i.v.)-potentiating effect of Haloperidol (5 mg/kg i.p.) was determined according to Borsy et al. (Acta Physiol. 27, 65–80 /1965/).

A group of the new compounds according to the invention exerts hypotensive effect on anesthetized animals in low dosages. Both the extent and the duration of effect of the new derivatives studied is superior to that of the reference substance (Dihydroergotamine). The hypotensive effect of the compounds is accompanied by bradycardia; they inhibit the vasomotor reflexes acting both at central and peripheral target structures. The mechanism of hypotensive effect is different in certain aspects from that of the hydrogenated ergot alkaloids; namely, the new derivatives have no or only negligible adrenolytic activity. Thus, the hypotensive effect is mainly due to an action exerted on the vasomotor center. These derivatives lower the blood pressure also in hypertensive animals upon oral administration. Thus, the compound described in Example 2 (6-methyl-8-[/N-methanesulfonyl, N-azidoethyl/-aminomethyl]-ergol-8-ene hydrogen maleate) given orally in doses of 1.0 to 2.5 mg/kg to awake spontaneously hypertensive rats lowered the blood pressure for several hours. The compounds according to the invention exert powerful hypotensive action also in cats. The experimental data obtained in the latter species are presented in Table 4.

TABLE 4

| | Hypotensive activity in cats | | |
|---|---|---|---|
| Compound (Example No.) | Dose (mg/kg) i.v. | Decrease of blood pressure (Δ mmHg) | Duration of action (hours) |
| 1 | 0.5 | −35 | 1.5–2 |
| 2 | 0.5 | −50 | 2 |
|   | 0.1 | −25 | 2 |
| 3 | 0.5 | −35 | 1.5 |
|   | 0.1 | −20 | 1.5 |
| 4 | 0.5 | −50 | 2 |
|   | 0.1 | −20 | 1.5 |
| 7 | 0.5 | −40 | 1 |
| 9 | 0.5 | −45 | 1 |
| 10 | 0.5 | −40 | 1.5 |
| 11 | 0.5 | −50 | 2 |
|   | 0.25 | −35 | 2 |
| Dihydroergotamine | 0.2 | −25 | 0.5 |

The measurements were performed in cats anesthetized with 30 mg/kg of Pentothal (5-ethyl-5-(1-methyl-butyl)-2-thiobarbituric acid sodium salt). The left femoral artery was cannulated; the arterial blood pressure was measured by means of Statham P 23 pressure transducer and registrated by a Hellige polygraph. The test compounds were injected into the right femoral vein. (Method: Mc Leod L. J., in: Pharmacological Experiments on Intact Preparations, E. S. Livingstone, Edinburgh and London, 1970, pp. 65–66.)

The new compounds of the general formula I and their pharmaceutically acceptable acid addition salts can be applied either as such or in the form of pharmaceutical compositions, such as tablets, coated tablets, capsules, suppositories, injectable solutions etc., suitable for enteral or parenteral administration. Of the salts the water-soluble ones are preferred. The pharmaceutical compositions are prepared by conventional methods, utilizing conventional inert organic or mineral carriers, such as lactose, starch, talc, stearic acid, water, alcohols, natural and hardened oils, waxes etc. and/or auxiliary agents, such as preservatives, stabilizing agents, wetting agents, dissolution aids, sweeting agents, dyestuffs, flavouring agents, etc.

The invention is elucidated in detail by the aid of the following non-limiting Examples.

EXAMPLE 1

6-Methyl-8-[(N-methanesulfonyl, N-methanesulfonyloxyethyl)-aminomethyl]-ergol-8-ene hydrogen maleate 2.97 g of 6-methyl-8-[(2-hydroxyethyl)-aminomethyl]-ergol-8-ene are dissolved in 700 ml of anhydrous pyridine under stirring. The solution is cooled to 0°–5° C., then 2.29 g of methanesulfonic acid chloride dissolved in 5 ml of acetonitrile are added in 10 minutes. The reaction mixture is stirred for one hour at the temperature indicated above, thereafter for 3 hours at room temperature. The progress of reaction is monitored by thin-layer chromatography using DC-Alufolien Kieselgel 60 /5553/ /Merck, Darmstadt, FRG/ plate and a mixture of chloroform:water:ethanol = 100:0.75:20. The chromatogram is processed by van Urk reagent. After the completion of the reaction, the reaction mixture containing pyridine is poured into 200 ml of icy water and 500 ml chloroform are added. After shaking the mixture the pH of the aqueous solution is adjusted to 7.5 with 2% aqueous sodium carbonate solution. After repeated shaking the organic phase is separated and the aqueous phase is extracted three times with 100 ml of chloroform each. The chloroform fractions are combined, dried over sodium sulfate and evaporated to dryness in vacuo. The residue is dissolved in a 100:0.3:12 mixture of chloroform, water and ethanol, then subjected to column chromatography. 60 g of silica gel /Woelm, 63–200/ are applied as adsorbent, and the column is eluted with the same solvent mixture. The effluent is analyzed by thin layer chromatography. The fractions containing a substance with an $R_f$ value of 0.75 are combined, evaporated in vacuo and the residue is treated with an alcoholic solution of maleic acid to form the salt. 4.55 g of 6-methyl-8-[(N-methanesulfonyl, N-methanesulfonyloxy-ethyl)-aminomethyl]-ergol-8-ene hydrogen maleate are obtained. Yield: 71%; m.p.: 158°–160° C.; $/\alpha/_D^{20} = -33.5°/c=0.5$; in 50% aqueous ethanol/.

EXAMPLE 2

6-Methyl-8-[(N-methanesulfonyl, N-azidoethyl)-aminomethyl]-ergol-8-ene hydrogen maleate 4.43 g of free base liberated from the product of Example 1 are dissolved in the mixture of 70 ml of methylcellosolve and 7 ml of water under stirring. When the solid dissolves 2.34 g of sodium azide are added, then the mixture is refluxed by boiling for 2 hours. The progress of the reaction is monitored by thin layer chromatography as described in Example 1. After the completion of reaction the solution is evaporated to dryness in vacuo, then the residue is dissolved in the mixture of 150 ml of water and 100 ml of chloroform. The mixture is shaken, the chloroform phase is separated and the aqueous phase is extracted four times with 100 ml of chloroform each. The chloroform fractions are combined, dried, filtered off and evaporated to dryness in vacuo. The raw product is dissolved in the eluting solvent (see below) and subjected to column chromatography, applying 60 g of silica gel as adsorbent. The column is eluted with a 100:0.75:20 mixture of chloroform, water and ethanol. The fractions containing a substance with an $R_f$ value of 0.85 are combined and evaporated in vacuo. The residue is treated with an alcoholic solution of maleic acid to form the salt. 4.23 g of 6-methyl-8-[(N-methanesulfonyl, N-azidoethyl)-aminomethyl]-ergol-8-ene hydrogen maleate are obtained. Yield: 82.0%; m.p. = 158°–160° C.; $/\alpha/_D^{20} = -39.6°$ /c=0.5; in 50% aqueous ethanol/.

EXAMPLE 3

2-Bromo-6-methyl-8-[(N-methanesulfonyl, N-azidoethyl/aminomethyl]-ergol-8-ene hydrogen maleate 4.0 g of free base liberated from the product of Example 2 are dissolved in 140 ml of anhydrous, peroxyde-free dioxane under stirring at room temperature, and 1.8 g of N-bromo-succinimide dissolved in 10 ml of dioxane are slowly added (within 30 minutes). The reaction mixture is stirred at room temperature for 3 hours. The progress of the reaction is monitored by thin layer chromatography as described in Example 1. The chromatogram is processed by iodine vapour. After the termination of the reaction the reaction mixture is diluted with 210 ml of water, shaken with 500 ml of chloroform and then the pH of the mixture is adjusted to 8.0 with aqueous ammonia. After repeated shaking the chloroform phase is separated and the aqueous phase is extracted four times with 100 ml of chloroform at pH 8.0. The chloroform fractions are combined, dried over sodium sulfate, filtered off and evaporated to dryness in vacuo. The residue is dissolved in the eluting solvent (see below) and subjected to column chromatography applying 60 g of silica gel as adsorbent. The column is eluted with 2% ethanol in chloroform. The effluent is analyzed by thin layer chromatography. The fractions containing a substance with an $R_f$ value of 0.45 are combined, evaporated in vacuo and the residue is treated with an alcoholic solution of maleic acid to form salt. 3.76 g of 2-bromo-6-methyl-8-[(N-methanesulfonyl, N-azidoethyl)-aminomethyl]-ergol-8-ene hydrogen maleate are obtained. Yield: 63.0%; m.p.=161°–163° C.; $/\alpha/_D^{20}$ base=−155.6° /c=0.1; in pyridine/.

EXAMPLE 4

1,6-Dimethyl-8-[(N-methanesulfonyl, N-azidoethyl/aminomethyl]-ergol-8-ene tartarate One proceeds as described in Example 2 with the difference that 4.6 g of 1,6-dimethyl-8-[(N-methanesulfonyl, N-methanesulfonyloxy-ethyl)-aminomethyl]-ergol-8-ene are applied as starting substance. The resulting base is treated with a methanolic solution of tartaric acid to form the salt. 3.3 g of 1,6-dimethyl-8-[(N-methanesulfonyl, N-azidoethyl)-aminomethyl]-ergol-8-ene tartarate are obtained. Yield: 59%; m.p.=168°–170° C.; $/\alpha/_D^{20}$=−80.2° /c=0.1; in pyridine/.

EXAMPLE 5

2-Bromo-1,6-dimethyl-8-[(N-methanesulfonyl, N-azidoethyl/-aminomethyl]-ergol-8-ene tartarate One proceeds as described in Example 3 with the difference that 4.14 g of 1,6-dimethyl-8-[(N-methanesulfonyl, N-azidoethyl)-aminomethyl]-ergol-8-ene are applied as starting substance. The resulting base is treated with a methanolic solution of tartaric acid to form the salt. 4.37 g of 2-bromo-1,6-dimethyl-8-[(N-methanesulfonyl, N-azidoethyl)-aminomethyl]-ergol-8-ene tartarate are obtained. Yield: 68.0%; m.p.=111°–113° C.; $/\alpha/_D^{20}$=−93.75° /c=0.1; in pyridine/.

EXAMPLE 6

6-Methyl-8-[(N-methanesulfonyl, N-methanesulfonyloxyethyl)-aminomethyl]-ergoline hydrogen maleate One proceeds as described in Example 1 with the difference that 3.0 g of 6-methyl-8-[(2-hydroxyethyl)-aminomethyl]-ergoline are applied as starting substance. 4.11 g of 6-methyl-8-[(N-methanesulfonyl-N-methanesulfonyloxy-ethyl)-aminomethyl]-ergoline hydrogen maleate are obtained. Yield: 72%; m.p.=138°–140° C.; $[\alpha]_D^{20}$=−31.0° /c=0.5; in 50% aqueous ethanol/.

EXAMPLE 7

6-Methyl-8-[(N-methanesulfonyl, N-azidoethyl)-aminomethyl]-ergoline hydrogen maleate One proceeds as described in Example 2 with the difference that 4.55 g of 6-methyl-8-[(N-methanesulfonyl, N-methanesulfonyloxy-ethyl)-aminomethyl]-ergoline are applied as starting substance. 3.1 g of 6-methyl-8-[(N-methanesulfonyl, N-azidoethyl)-aminomethyl]-ergoline hydrogen maleate are obtained. Yield: 60%; m.p.=160°–162° C.; $[\alpha]_D^{20}$=−38.94° /c=0.5; in 50% aqueous ethanol/.

EXAMPLE 8

1,6-Dimethyl-8-[(N-methanesulfonyl, N-methanesulfonyloxy-ethyl)-aminomethyl]-ergoline hydrogen maleate One proceeds as described in Example 1 with the difference that 3.15 g of 1,6-dimethyl-8-[(2-hydroxyethyl)-aminomethyl]-ergoline are applied as starting substance. 3.7 g of 1,6-dimethyl-8-[N-methanesulfonyl, N-methanesulfonyloxy-ethyl)-aminomethyl]-ergoline hydrogen maleate are obtained. Yield: 64.0%; m.p. 112°–114° C.; $[\alpha]_D^{20}$=−38.42 /c=0.5; in 50% aqueous ethanol/.

EXAMPLE 9

1,6-Dimethyl-8-[(N-methanesulfonyl, N-azidoethyl/aminomethyl]-ergoline hydrogen maleate One proceeds as described in Example 2 with the difference that 4.6 g of 1,6-dimethyl-8-[(N-methanesulfonyl, N-methanesulfonyloxy-ethyl)-aminomethyl]-ergoline are applied as starting substance. 3.08 g of 1,6-dimethyl-8-[(N-methanesulfonyl, N-azidoethyl)-aminomethyl]-ergoline hydrogen maleate are obtained. Yield: 58.0%; m.p.=155°–157° C.; $[\alpha]_D^{20}$=−47.7° /c=0.5; in 50% aqueous ethanol/.

EXAMPLE 10

2-Bromo-1,6-dimethyl-8-[(N-methanesulfonyl, N-azidoethyl)-aminomethyl]-ergoline tartarate One proceeds as described in Example 3 with the difference that 4.16 g of 1,6-dimethyl-8-[(N-methanesulfonyl, N-azidoethyl)-aminomethyl]-ergoline are applied as starting substance. The resulting base is treated with a methanolic solution of tartaric acid to form the salt. 3.05 g of 2-bromo-1,6-dimethyl-8-[(N-methanesulfonyl, N-azidoethyl)-aminomethyl]-ergoline tartarate are obtained.

Yield: 47.0%, m.p.=213°–215° C.; $[\alpha]_D^{20}$=−60.1° /c=0.1; in pyridine/.

EXAMPLE 11

6-Methyl-8-[(ethanesulfonyl, N-ethanesulfonyloxyethyl)-aminomethyl]-ergol-8-ene 2.97 g of 6-methyl-8-[(2-hydroxyethyl)-aminomethyl]-ergol-8-ene are dissolved in 700 ml of anhydrous pyridine under stirring. The solution is cooled to 0°–5° C., and 2.56 g of ethanesulfonic acid chloride dissolved in 5 ml of acetonitrile are added dropwise in 10 minutes. Otherwise one proceeds as described in Example 1 with the difference that the product is separated as base. 2.35 g of 6-methyl-8-[(N-ethanesulfonyl, N-ethanesulfonyloxyethyl)-aminomethyl]-ergol-8-ene are obtained. Yield: 49.0%; m.p.=95°–97° C.; $[\alpha]_D^{20}$=−84.9° /c=0.1; in pyridine/.

EXAMPLE 12

6-Methyl-8-[(N-ethanesulfonyl, N-ethanesulfonyloxy-ethyl)-aminomethyl]-ergoline

One proceeds as described in Example 11 with the difference that 3.0 g of 6-methyl-8-[(2-hydroxyethyl)-aminomethyl]-ergoline are applied as starting substance. 2.55 g of 6-methyl-8-[(N-ethanesulfonyl, N-ethanesulfonyloxy-ethyl)-aminomethyl]-ergoline are obtained. Yield: 53.0%; m.p.=153°-154° C.; [α]$_D^{20}$=−53.9° /c=0.5; in pyridine/.

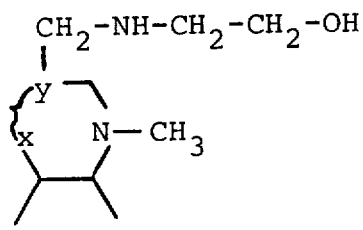

We claim:

1. New ergol-8-ene and ergoline derivatives of general formula /I/

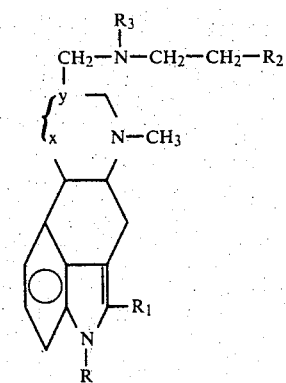

wherein $\overline{xy}$ stands for —CH=C= or —CH$_2$—CH= group,
R stands for hydrogen atom or methyl group,
R$_1$ stands for hydrogen or halogen atom,
R$_2$ stands for lower alkylsulfonyloxy group, phenylsulfonyloxy group optionally substituted with a lower alkyl group, or azido group,
R$_3$ stands for lower alkylsulfonyloxy group or phenylsulfonyloxy group optionally substituted with a lower alkyl group,
and acid addition salts thereof.

2. 6-methyl-8-[(N-methanesulfonyl, N-methanesulfonyloxy-ethyl)-aminomethyl]-ergol-8-ene and acid addition salts thereof.

3. 6-Methyl-8-[(N-methanesulfonyl, N-azidoethyl)-aminomethyl]-ergol-8-ene and acid addition salts thereof.

4. 2-Bromo-1,6-dimethyl-8-[(N-methanesulfonyl, N-azidoethyl)-aminomethyl]-ergoline and acid addition salts thereof.

5. A pharmaceutical composition for dopamine receptor stimulant activity which comprises a pharmaceutically acceptable carrier or diluent and an effective amount of at least one compound of the formula I of claim 1.

* * * * *

UNITED STATES PATENT AND TRADEMARK OFFICE
CERTIFICATE OF CORRECTION

PATENT NO. : 4,299,836

DATED : November 10, 1981

INVENTOR(S) : ERZSÉBET MAGÓ née KARÁCSONY ET AL.

It is certified that error appears in the above—identified patent and that said Letters Patent is hereby corrected as shown below:

IN THE ABSTRACT:

First line, after Formula II, "x y" should be corrected to read: -- $\widehat{x\ y}$ --.

Signed and Sealed this

Twenty-sixth Day of January 1982

[SEAL]

Attest:

Attesting Officer

GERALD J. MOSSINGHOFF

Commissioner of Patents and Trademarks

UNITED STATES PATENT AND TRADEMARK OFFICE
CERTIFICATE OF CORRECTION

PATENT NO. : 4,299,836

DATED : November 10, 1981

INVENTOR(S) : ERZSÉBET MAGÓ née KARÁCSONY ET AL.

It is certified that error appears in the above—identified patent and that said Letters Patent is hereby corrected as shown below:

IN THE ABSTRACT:

That portion of Formula II which is

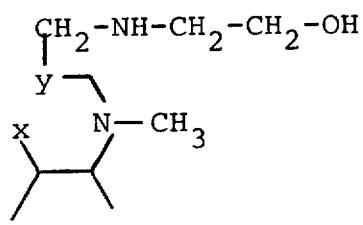

should be corrected to read